(12) United States Patent
Haran et al.

(10) Patent No.: US 7,291,856 B2
(45) Date of Patent: Nov. 6, 2007

(54) SENSOR AND METHODS FOR MEASURING SELECT COMPONENTS IN MOVING SHEET PRODUCTS

(75) Inventors: Frank M. Haran, North Vancouver (CA); Ronald E. Beselt, Burnaby (CA)

(73) Assignee: Honeywell International Inc., Morristown, NJ (US)

( * ) Notice: Subject to any disclaimer, the term of this patent is extended or adjusted under 35 U.S.C. 154(b) by 77 days.

(21) Appl. No.: 11/116,498

(22) Filed: Apr. 28, 2005

(65) Prior Publication Data

US 2006/0243931 A1 Nov. 2, 2006

(51) Int. Cl.
*G01N 15/06* (2006.01)
*G01N 21/49* (2006.01)
*G01N 21/85* (2006.01)
*G01J 1/04* (2006.01)
*G01J 1/32* (2006.01)

(52) U.S. Cl. .................. 250/574; 250/227.16; 250/205

(58) Field of Classification Search ............... 250/205, 250/559.19, 559.2, 559.25, 559.27, 574, 250/339.01, 339.1; 356/402–425
See application file for complete search history.

(56) References Cited

U.S. PATENT DOCUMENTS

| | | | |
|---|---|---|---|
| 4,006,358 A | 2/1977 | Howarth | 250/339 |
| 4,288,691 A | 9/1981 | Horton | 250/281 |
| 4,376,946 A | 3/1983 | Kaminow et al. | 357/17 |
| 4,592,043 A | 5/1986 | Williams | 370/3 |
| 4,634,928 A | 1/1987 | Figueroa et al. | 313/499 |
| 4,786,817 A * | 11/1988 | Boissevain et al. | 250/559.01 |
| 4,807,630 A | 2/1989 | Malinouskas | |
| 4,856,014 A | 8/1989 | Figueroa et al. | 372/46 |
| 4,883,963 A * | 11/1989 | Kemeny et al. | 250/339.11 |
| 4,928,013 A | 5/1990 | Howarth et al. | 250/339 |
| 5,015,099 A * | 5/1991 | Nagai et al. | 356/437 |
| 5,122,974 A | 6/1992 | Chance | |
| 5,235,192 A | 8/1993 | Chase et al. | 250/571 |
| 5,313,187 A | 5/1994 | Choi et al. | 340/331 |
| 5,338,361 A | 8/1994 | Anderson et al. | 118/689 |
| 5,400,258 A | 3/1995 | He | 364/471 |
| 5,774,213 A | 6/1998 | Trebino et al. | |
| 5,795,394 A | 8/1998 | Belotserkovsky et al. | 118/665 |
| 5,821,536 A | 10/1998 | Pettit | |
| 6,074,483 A | 6/2000 | Belotserkovsky et al. | 118/665 |
| 6,466,839 B1 | 10/2002 | Heaven et al. | 700/128 |
| 6,556,305 B1 | 4/2003 | Aziz et al. | 356/512 |
| 6,724,473 B2 | 4/2004 | Leong et al. | 356/237.2 |

(Continued)

FOREIGN PATENT DOCUMENTS

EP 0319158 6/1989

(Continued)

*Primary Examiner*—Patrick J. Lee
(74) *Attorney, Agent, or Firm*—Munck Butrus, P.C.

(57) ABSTRACT

A compact, long lasting sensor for measuring components such as moisture in moving sheets including paper in a papermaking apparatus employs light sources that produce radiation within defined wavelength regions of interest and the light sources are modulated at high frequencies using non-mechanical techniques. A single detector with various radiation sources can measure at all frequencies while keeping information separated. Superluminescent light emitting diode or laser diode light sources can be directly electrically modulates for improved noise rejection. These higher power and bright light sources afford excellent fiber optic launch efficiency and permits the sensor to be scanned at much faster rates over the paper being monitored.

31 Claims, 8 Drawing Sheets

U.S. PATENT DOCUMENTS

| | | |
|---|---|---|
| 6,743,337 B1 | 6/2004 | Ischdonat |
| 6,763,322 B2 | 7/2004 | Potyrailo et al. ............ 702/189 |
| 6,805,899 B2 | 10/2004 | MacHattie et al. ............. 427/8 |
| 6,856,436 B2 | 2/2005 | Brukilacchio et al. ....... 359/196 |
| 6,949,734 B2 * | 9/2005 | Neff et al. ................... 250/226 |
| 2004/0119781 A1 | 6/2004 | Szumla |
| 2004/0212804 A1 | 10/2004 | Neff et al. |
| 2004/0260520 A1 | 12/2004 | Braendle et al. |
| 2005/0065400 A1 | 3/2005 | Banik et al. |

FOREIGN PATENT DOCUMENTS

| | | |
|---|---|---|
| EP | 1491877 | 12/2004 |
| WO | WO 03/037111 | 5/2003 |

* cited by examiner

SENSOR AND METHODS FOR MEASURING SELECT COMPONENTS IN MOVING SHEET PRODUCTS

FIELD OF THE INVENTION

The present invention generally relates to high-speed, long-life sensors and methods for measuring the presence and concentrations of specific components such as moisture in paper and other sheet products. The technique employs a device that directs infrared radiation from a superluminescent light emitting diode (SLED) or laser diode (LD) within specific wavelength bands onto a moving sheet of material and detects the radiation which emerges from the material.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Papermaking devices well known in the art are described for example in Handbook for Pulp & Paper Technologists 2nd ed., G. A. Smook, 1992, Angus Wilde Publications, Inc., and Pulp and Paper Manufacture Vol III (Papermaking and Paperboard Making), R. MacDonald, ed. 1970, McGraw Hill. Sheetmaking systems are further described, for example, in U. S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al. Many factors influence the rate at which water is removed which ultimately affects the quality of the paper produced.

In the art of modem high-speed papermaking, it is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge. For example, a high-speed scanning sensor may complete a scan in a period as short as twenty seconds, with measurements being read from the sensor at about 10 milliseconds intervals. A series of stationary sensors can also be used to make similar on-line measurements.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infrared (IR) region. A monitoring or gauge apparatus for this purpose is commonly in use. Such apparatus conventionally uses either a fixed gauge or a gauge mounted on a scanning head which is repetitively scanned transversely across the web at the exit from the dryer section and/or upon entry to the take up reel, as required by the individual machines. The gauges typically use a broadband infrared source such as a quartz tungsten halogen (QTH) lamp and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (typically called "reflective" type) in which the source and detector are in a single head on one side of the web, the detector responding to the amount of source radiation scattered from the web.

Although it is most common to position IR moisture gauges in the more benign dry-end environment, similar gauges are also employed in the wet-end of the papermaking machine. The wet-end moisture gauges are typically located at the end of the press section or the beginning of the dryer section. Gauges in these locations are useful for diagnosis of press and forming sections of the paper machine, or for "setting up" the web for entry into the dryer section.

The speed of current IR moisture sensors is limited by the requirement to mechanically modulate the source light. For detecting moisture in paper, sensors typically utilize light with wavelengths at 1.9 µm (measure) and 1.8 µm (reference). At present, sufficiently powerful reliable, and economical sources at these wavelengths are only achievable using QTH lamps which can be modulated to up to 10,000 Hz by mechanical means, but in practice are modulated at less than 1 kHz. Mechanical modulation is limited to these lower frequencies because increasing the modulation frequency entails reducing the aperture and hence limiting either the power or the modulation depth. Furthermore, the mechanical tolerance requirements required to obtain acceptable jitter on the modulation become unachievable. These sources also exhibit limited output brightness (power per unit area per unit solid angle) and typically have lifetimes of only a few thousand hours. The limited brightness of these thermal sources makes for very poor coupling efficiency into optical fibers and also limits the accurate measurement of small sample areas. To date, all known IR moisture sensors for paper and flat sheet products use QTH lamps as sources. The practical mechanical modulation frequency used with QTH lamps limits the sensor bandwidths to around 100 to 500 Hz.

SUMMARY OF THE INVENTION

The present invention is based in part on the development of a very high-speed, compact, long-lifetime sensor that is particularly suited for measuring components such as moisture in moving sheets including paper in a papermaking apparatus. The sensor employs light sources that only produce radiation within defined wavelength regions of interest and the sources are modulated at high frequencies using non-mechanical techniques. In contrast to conventional sensors which use at least two light detectors per sensor, the inventive sensor only requires a single detector where each of the spectral channels is modulated at a different frequency thereby keeping their information separated. Since the sensor does not require light sources with all necessary wavelengths in them, i.e., broadband sources, no band pass filters are needed as in conventional moisture sensors. Besides eliminating the need for two detectors with their own individual filters, much duplication in the electronics can also be eliminated. For example, only one trans-impedance pre-amplifier is required. The use a single detector and common electrical circuitry between the reference and measure wavelength channels of a typical sensor also helps tremendously with common mode rejection of some noise effects in the channels. For example, when separate detectors are used, then differential temperature drift between detectors could produce a sensor error, but when only one detector element (and common circuitry) is used, a proportion of this effect is eliminated.

In one embodiment, the invention is directed to a sensor, for measuring at least one selected component in a composition, that includes:
- at least one light source that generates light having a desired wavelength range to detect a component in the composition wherein the at least one light source is configured to direct the light to the composition;
- drive means for modulating the at least one light source, with the proviso that the drive means does not mechanically modulate the at least one light source; and
- detection means for receiving light that emerges from the composition.

In another embodiment, the invention is directed to an apparatus, for measuring at least one selected component in a composition, that includes:
- at least one light source that generates light having a desired wavelength range to detect a component in the composition wherein the at least one light source is configured to be delivered to a plurality of positions on the composition;
- drive means for modulating the at least one light source, with the proviso that the drive means does not mechanically modulate the at least one light source; and
- a plurality of detection means for receiving light that emerges from the composition at the plurality of positions.

In a further embodiment, the invention is directed to a method for sensing a substance in a composition that includes the steps of:
(a) irradiating the composition with radiation including wavelengths in at least first and second separate wavelength regions wherein the radiation is provided by light sources that are modulating non-mechanically, wherein radiation in the first wavelength region is strongly sensitive to the substance in the composition and radiation in the second wavelength region is less sensitive to the substance in the composition;
(b) detecting the amount of radiation that emerges from the composition in the first and second separate wavelength regions.

In a preferred embodiment, the light sources employed are SLEDs or LDs in which the drive currents are electrically modulated. Alternatively, external electro-optical or acousto-optical modulators can be employed to modulate the light sources. There are several reasons for modulating the light sources: (1) for use with lockin detection for signal-to-noise improvements as well as exclusion of background signals, and (2) for discriminating between source channels by modulating each channel at a different frequency, for example, by frequency division multiplexing, when more than one source are used. The high spatial mode quality of SLED or LD sources allows for efficient use of these types of modulation in single mode fiber optical devices, which is not possible with low brightness thermal sources such as QTH lamps, where single-mode fiber coupling is not practically possible.

SLED sources generate approximately 100 times more power in the moisture bandwidth and approximately 500,000 times the brightness in the moisture bandwidth than thermal light sources, e.g., broadband sources, used in conventional moisture sensors. The higher power and brightness of the light sources employed with the inventive sensor allow the sensor to be scanned much faster over the product, e.g., paper, being monitored and to achieve high spatial resolution. An additional benefit associated with the higher power and brightness levels attendant with SLEDs and LDs light sources is their excellent fiber optic launch efficiency. These solid state sources are compatible with single mode optical fibers and other components that are traditionally used in the telecommunications industry, therefore, the ability to use solid state light sources with single mode optical fibers and related components affords lower cost and higher efficiency sensor systems, which cannot be realized with thermal light sources such as QTH lamps.

Infrared spectroscopy is a preferred technique for moisture content measurements and one approach is to employ a sensor having SLEDs that emit IR radiation at the predetermined absorption and reference wavelengths of interest. While it is believed that no high power, reliable or stable SLED or LD source is currently commercially available at the 1.9 to 2.0 µm radiation range, another water sensitive absorption peak does exist in the 1.4 to 1.5 µm wavelength region. Although this absorption peak is less sensitive to moisture, there are some suitable high power and high-speed SLED and tunable LD optical sources available at these wavelengths. These light sources can be readily modulated from DC or continuous wave (CW) levels up to GHz rates which, in combination with their high-power output, enable the sensors to be more accurate and to operate at very high bandwidths. The ability to modulate at these much higher rates allows for better noise rejection in the output filter stage of lockin detection.

There are secondary advantages for using the 1.4 to 1.5 µm water absorption band over using the 1.9 to 2.0 µm water absorption band. These include lower in-fiber optic losses and higher performance of photodiode light detectors. For example, the noise equivalent power (NEP) of a typical InGaAs photodiode is an order of magnitude better at the 1.5 µm wavelength than it is at the 1.9 µm wavelength. Also, solid state detectors with internal gain, i.e. avalanche photodiodes (APD), are readily available at the 1.5 µm wavelength but are not available at the 1.9 µm wavelength. Moreover, hard clad silica (HCS) multimode optical fibers which have much higher numerical apertures, which decreases the fiber bend loss sensitivity of measurements, can be employed. The HCS fiber is also relatively inexpensive. Furthermore, the increased brightness of the inventive optical source permits less expensive, smaller core optical fibers to be used. These are much more reliable than larger core optical fibers when subjected to small bends.

The typical lifetime of an SLED or LD source is about 20 years, whereas a QTH lamp has a 4000 hour typical lifetime. With the present invention, the mechanical motors and chopper associated with QTH lamps have also been eliminated thereby reducing cost and complexity and increasing reliability of QTH lamp-based systems. In particular, for such systems, a separate sensor is typically needed for the phasing signal used in lockin detection electronics. This allows the light source to be switched off either electrically or mechanically with a shutter to block the light from the QTH lamp but the electronics continues to operate. This action is required for a background light level reading or to enable the lockin electronics to work with very low light levels. With the SLED or LD source of the present invention, this extra component and associated complexity are eliminated.

DETAILED DESCRIPTION OF PREFERRED EMBODIMENTS

The present invention relates to a sensor system for detecting properties of a composition, especially material that is in the form of a film, web or sheet. While the sensor will be illustrated in measuring moisture in paper, it is understood that the sensor can be employed to detect a variety of components in a number of different materials including, for example, coated materials, plastics, fabrics, and the like.

Figure 1:
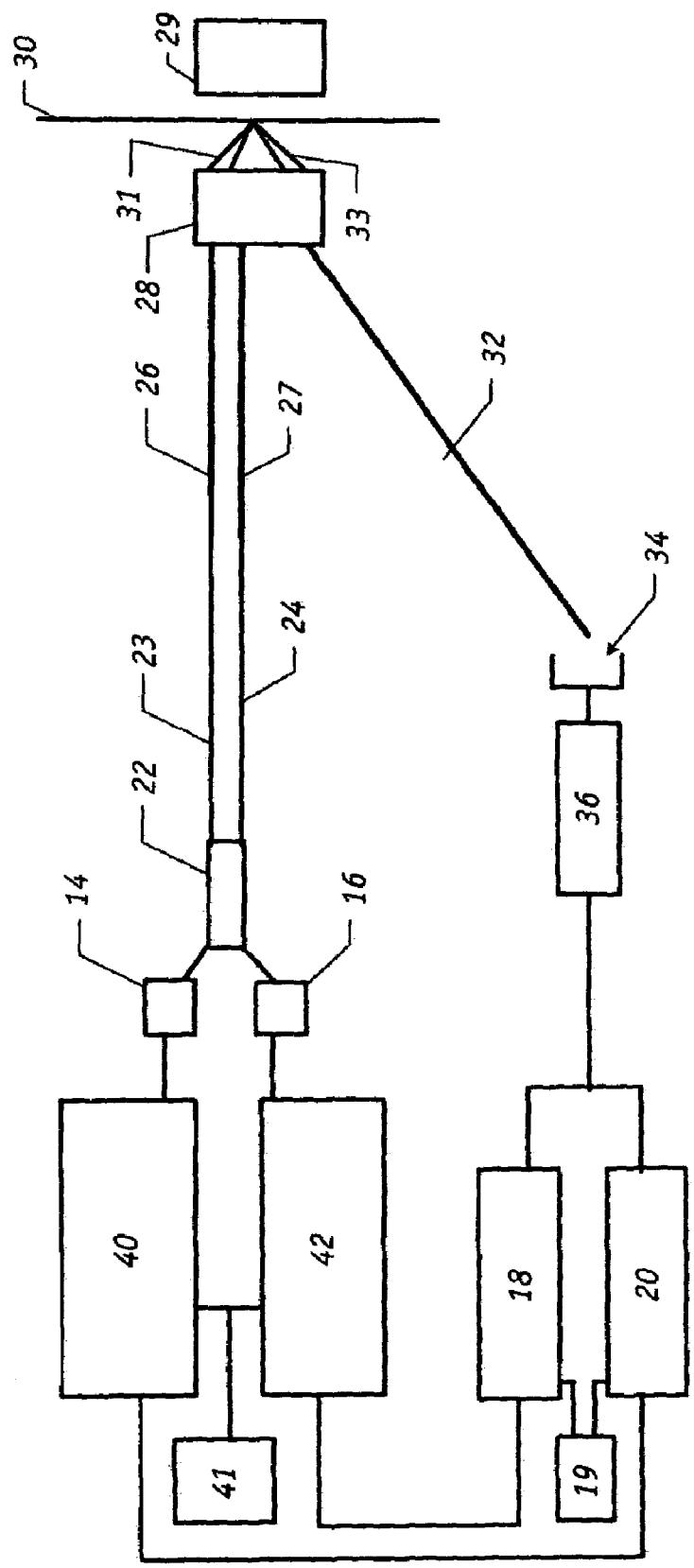
FIGS. 1 and 3 are schematic diagrams of two embodiments of the sensor apparatus of the present invention.

FIG. 1 is a schematic of a high-speed moisture sensor system that is particularly suited for measuring moisture in a moving sheet of paper. The system includes (i) a measurement (or absorption) wavelength light source controller 42 which modulates the measurement (or absorption) light source 16 and controls its temperature and (ii) a reference wavelength light source controller 40 which modulates the reference light source 14 and controls its temperature. The light sources preferably have a built-in temperature controlling device such as a Peltier cooler. Power source 41 is connected to controllers 40 and 42. Light sources 14 and 16 are coupled by a single mode optical fiber directional coupler 22 to multimode graded index optical fibers 23 and 24. The multimode graded optical fibers 23 and 24 are connected to the distal end of multimode step index optical fibers 26 and 27, respectively, which in turn are connected at their proximal ends to a probe or optical head 28.

A moving sheet 30 of material such as paper which is being monitored is preferably positioned adjacent the optical head 28 so that light 31 can be directed from the optical head 28 to the sheet 30. Some of the reflected light 33 is collected by the optical head 28. The optical head 28 is also connected to a multimode optical fiber 32 which delivers reflected light from the optical head 28 to a detector 34 that is preferably a PIN InGaAs photodiode. In this fashion, multimode optical fibers 26 provide a source beams and multimode optical fiber 32 provides a detector beam. The system further includes a transimpedance pre-amplifier 36, reference wavelength lockin amplifier 20, and measurement wavelength lockin amplifier 18. A computer 19 is employed for data signal analysis. The transimpedance pre-amplifier 36 serves to convert the photo-induced current from the PIN photodiodes 34 to a voltage signal for input to the lockin amplifiers 18, 20; in some cases the transimpedance amplifiers can be an integral part of the lockin amplifiers. The reference wavelength amplifier 20 and the measurement wavelength lockin amplifier 18 serve to extract low level modulated signals from the background by simultaneously amplifying the modulated signal, converting it to a proportionate DC level signal and suppressing the unmodulated background noise by passing the resulting signal through a low-pass filter; this output low-pass filter has a cut-off frequency preferably of at least 2 to 3 times lower than that of the modulation frequency and is typically at least 10 times lower than the modulation frequency. The larger the frequency difference between the low-pass output filter and the modulation frequency, the better the noise performance of the lockin detection. In contrast, with the limited 1 kHz QTH lamp source modulation, the lockin performance is extremely limited which is not the case with the present invention that employs the high-frequency modulation capabilities of the SLED or LD sources. The waveforms from the internal oscillators of the lockin amplifiers 18, 20 are used as reference waveforms for the light source controllers 42, 40 to modulated the photo-output of the light sources 14, 16.

Light from reference light source 14 and measurement light source 16 can be conveniently managed and transmitted through the common optical fibers 23 and 24 by multiplexing. A preferred technique is frequency division multiplexing (FDM). Suitable multiplexers and demultiplexers can be employed at the proximal and distal ends of the optical fibers 23 and 24. To implement FDM, the measurement and reference light sources 14 and 16 are modulated at different frequencies by controllers 40 and 42, respectively. A benefit to implementing multiplexing is that since each light source is modulated at a different frequency and only a single detector 34 and pre-amplifier 36 are needed to detect both wavelengths.

The sensor system is preferably employed to monitor paper quality by scanning the apparatus over a moving sheet of paper during production. The optical head 28 would move continuously back-and-forth along a cross direction relative to the moving sheet. The number of components in the optical head 38 are kept to a minimum to include the head-essential optical elements that are needed for delivery and collection of light to and from the sheet. The light source and other devices of the detection system such as the signal processing components and fiber couplers are located in a more benign environment in a location that is remote from the hostile environment that is usually associated with the sheet making process. The remote processor compartment is therefore away from the optical head that traverses back-to-forth over the sheet. The weight of the optical head is preferably less than one kilogram and more preferably less than 200 grams. In this case, the optical fibers 23, 24, 26, 27 and 32 can be part of a cable take-up mechanism that moves in tandem with the optical head 28. The purpose of the cable take-up mechanism is to manage the fiber optic while the optical head 38 is being moved as well as to preserve the overall bend length and radius.

The sensor system illustrated in FIG. 1 operates in the reflective mode in that it measures radiation that is reflected from the sheet being monitored. Alternatively, the sensor system can be readily modified to measure the intensity of radiation that is transmitted through the sheet 30. In this transmissive mode, the system can employ a detector 29, which is positioned on the opposite side of sheet 30, to detect radiation which passes through the sheet 30. The optics of detector 29 would be connected to optical fiber 32. In either case, the amount of moisture in the sheet 30 can be determined by detecting the light which emerges from, i.e., reflected from or transmitted through, a sheet 30 at the measurement, i.e., absorption, and reference band wavelengths.

When employing the sensor system to detect moisture content, one approach is to predetermine the absorption and reference IR wavelengths of interest and to employ the sensor to provide a constant, reliable, stream of energy within the wavelengths required to yield suitable water weight measurements. Specifically, water absorbs radiation across the infrared spectrum as a function of wavelength. The higher the moisture content in a sheet, the less radiation at or near the water absorption peak that will emerge from the sheet. A water sensitive absorption peak exists in the 1.9 to 2.0 μm radiation range and another water sensitive absorption peak exists around the 1.4 to 1.5 μm radiation range.

The sensor can simultaneously measure the intensity of radiation that emerges, i.e., reflected from or transmitted, from a sheet of paper using the absorption and reference IR band wavelengths. In effect, the absorption measurement at the adsorption IR band wavelength is primarily sensitive to the amount of water in the sheet and more IR radiation is measured when the sheet is dry and less infrared radiation when the sheet is moist. Conversely, for the reference measurement, the radiation is in an IR band wavelength where there is less moisture absorption. The light lost in this band is due to non-water dependent losses from the sheet. These losses are primarily due to scattering from the sheet as well as non-water dependent attenuation factors of the sheet. The reference measurement corrects for non-water dependent losses from the sheet. In this system, the reference wavelength can also correct for other common mode optical losses that are not moisture dependent such as the bend loss in the optical fibers. This is possible because both the measurement and reference wavelengths are subject to the same fiber bend after the fiber optical directional couple 22. Note that it is advantageous to have a reference wavelength that is close to the measurement wavelength while remaining outside the water absorption band.

Figure 2:
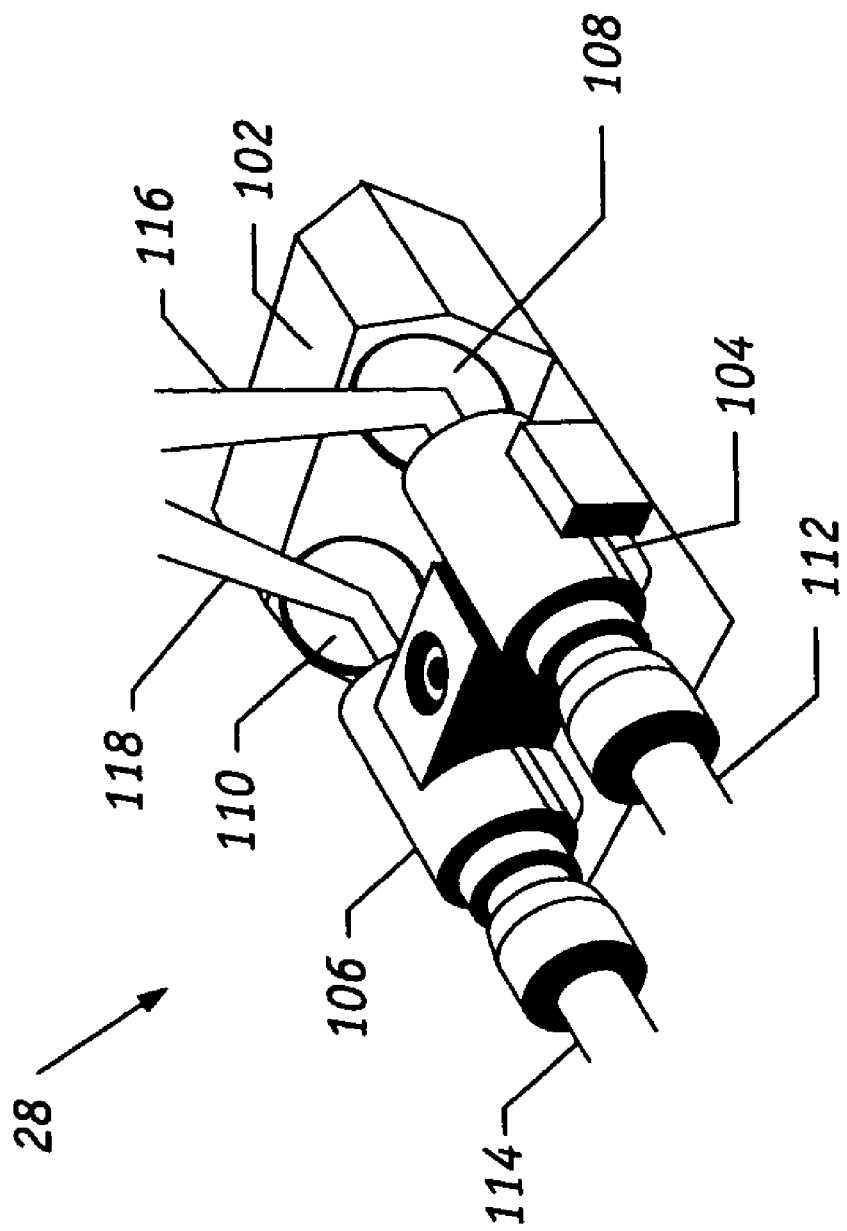
FIG. 2 illustrates an optical head.

As shown in FIG. 2, a suitable optical head 28 comprises a body 102 with couplers 104 and 106, which incorporate imaging lenses, for connecting optical fiber 112 that delivers a source beam and optical fiber 114 that delivers a detector beam, respectively. The optical head may optionally comprise a housing that protects it from the environment. Light 116 that is delivered from the optical fiber 112 is reflected from a turning mirror 108 and onto the sheet of material being scanned. Appropriate focusing lenses (not shown) can be employed. Scattered light 118 from the sheet is reflected from the mirror 110 and into the detector beam optical fiber 114. The contours of mirrors 108 and 110 can be fashioned so that light can be imaged onto and then captured from appropriate orientations relative to the moving sheet being scanned; in this case, the focusing lenses (not shown) can be omitted. The mirror's reflective surface can comprise a layer of gold, silver, aluminum, dielectric or other suitable reflective material.

Each of the measurement and reference light sources 40, 42, as shown in FIG. 1, provides a constant stream of energy within a wavelength required for measurement, in addition, the stream of energy from each light source can be amplitude modulated without devices such as a choppers, shutters, tuning forks and the like, which "mechanically modulate" the light source by physically disrupting the flow of radiation from the light source. With the present invention, the light sources are subject to non-mechanical modulation such as by direct modulation of the drive currents that are connected to the light sources. Other exemplary modulating techniques employ electro-optical modulators such as Kerr cells and Pockels cells that are positioned in the light beam path of the light source or acousto-optical devices such as acoustical optical tunable filters. These modulators of the in-fiber type are typically used in high-speed telecommunication systems. The inventive light source can be efficiently coupled into single-mode optical fibers. Typically, the light sources are modulated at a rate of higher than 1,000 Hz, preferably at a rate of at least 5 KHz and more preferably to at least 20 kHz to 1 MHz and higher. A preferred light source device is a light-emitting diode operating at relatively high powers and having a relatively broad spectral width that are known as superluminescent light-emitting diodes (SLED). SLED sources differ from conventional LED sources in that the former have an extremely small emitting area divergence product, i.e., a high brightness, which allows them to be efficiently launched into single mode fiber. The SLED, which has a long-lifetime of typically 20 years can be directly modulated via a drive current at high frequencies. The SLED can also use external fiber modulators that modulate at GHz frequencies.

SLED sources generating light in the 0.7 to 1.6 μm wavelength range are commercially available and the light typically has a FWHM (Full Width Half Maximum) linewidth in the order of 50 nm. Because SLEDs generate light of extremely high brightness, they can typically deliver 2-45 mW of power into a single mode optical fiber. With respect to the measurement light source for measuring moisture in paper, currently available SLED sources only operate around the less sensitive 1.4 to 1.5 μm wavelength band and not at 1.9 μm. In terms of the reference light source, commercially available SLEDs that operate at 0.83, 0.93, 1.3 or 1.55 μm can be employed. In either case, no interference filters are needed, that is, the sensors can simply utilize the natural linewidths of measurement and reference SLED light sources. In this fashion, much more of the energy that is transmitted through the optical fibers is used for detection as compared to prior devices that employ light from a broadband light source. As stated previously, there are a number of secondary advantages associated with using the 1.4 to 1.5 μm water absorption band over that of the 1.9 to 2.0 μm water absorption band including improved performance and lower costs. In addition, high numerical aperture HCS multimode optical fibers can be used.

Another light source for the inventive sensor is the laser diode. For sensing moisture in paper, a tunable laser source is preferred because the absorption peak of water is a function of temperature and a tunable laser diode enables the sensor to follow this absorption peak as the temperature of the paper being monitored fluctuates. For example, the sensitivity of the 1.9 μm absorption peak to temperature is approximately 0.3 nm/° C. The less sensitive 1.4 μm absorption peak has been measured to have a greater temperature sensitivity of 0.47 nm/° C. Solid state tunable laser sources in the 1.9 μm wavelength range based on a diode pumped Nd:YAG lasers pumping and optical parametric oscillator (OPO) are commercially available, however, currently these types of source are less preferred for economic or environmental sensitivity reasons. Tunable laser diodes that generate radiation in the 1.4 to 1.5 μm wavelength range are available, for instance, from New Focus (San Jose, Calif.).

When employed as light sources in the inventive sensor, fixed and tunable laser diode sources exhibit many of the same advantages associated with SLED sources except that with tunable laser diodes, temperature dependent wavelength shifting should be accounted for. The sensor can be readily optimized to adjust to the changing dynamics in the environment in which it operates. For example, it is known that the absorption or sensing center wavelength for moisture in paper is typically 1.93 μm and the reference wavelength is typically 1.84 μm at typical ambient conditions, but the absorption wavelength is temperature dependent.

Besides measuring moisture content, other physical characteristics of sheet material can also be monitored. For example, fibers, such as cellulose, latex, minerals, e.g., $CaCO_3$ and clay, and the like can be detected. In each case, selecting the proper radiation regions, e.g., measurement and reference IR bandwidths, is required. IR absorption by different components in paper and paper coated products are further described in U.S. Pat. No. 5,013,403 to Chase, U.S. Pat. No. 5,235,192 to Chase et al., and U.S. Pat. No. 5,795,394 to Belotserkovsky et al., which are incorporated herein by reference.

The inventive sensor system can also be used to measure the concentration of a polymer in films that are formed in a continuous plastic production process. For instance, sensor system can be employed with any suitable apparatus for continuous production of plastic films known in the art. Representative machines are further described, for instance, in U.S. Pat. No. 6,793,854 to Kirjavainen, U.S. Pat. No. 6,565,343 to Krycki, U.S. Pat. No. 5,230,923 to Hirokawa et al., U.S. Pat. No. 4,797,246 to Reinke et al., and U.S. Pat. No. 4,311,658 which are incorporated herein by reference. The sensor can be positioned anywhere along the production line as desired.

A preferred application of the sensor is to monitor the thickness of the film by measuring the concentration(s) (weights per unit area, typically measured in grams per square meter, gsm) of the particular polymer(s) that form the film. In the case where the film consists of a single layer of one polymer, the sensor is set to direct radiation, e.g., IR radiation, of the appropriate bandwidth to measure the polymer. In the case where the plastic is a single layer that comprises a blend of two or more different polymers or where the plastic is a multilayer film, multiple sensors can be employed or a sensor with multiplexed configuration can be employed to detect the various polymer components. Multilayer films typically comprise a plurality of layers that are laminated together. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The sensor of the present invention, among other things, is effective in controlling the production of multilayer films to assure that each layer in the film has the proper thickness or weight (gsm) so that the multilayer film has the right combination of properties.

The high-speed moisture sensor system can also be employed to measure moisture along the cross direction, machine direction, or both directions of a papermaking machine. As described above, the optical head 28 depicted in FIG. 1 can be scanned across a moving sheet. For measuring moisture in the machine direction (MD), it is preferred that a plurality of sensors be deployed at essentially in tandem at different MD locations but at the same cross direction (CD) location relative to the edges of the papermaking machine. In this fashion, a moisture MD profile is produced. As is apparent, individual sensor systems, each with at least two SLEDs, with their individual controllers, that generate the measurement and reference wavelengths can be employed.

Figure 3:
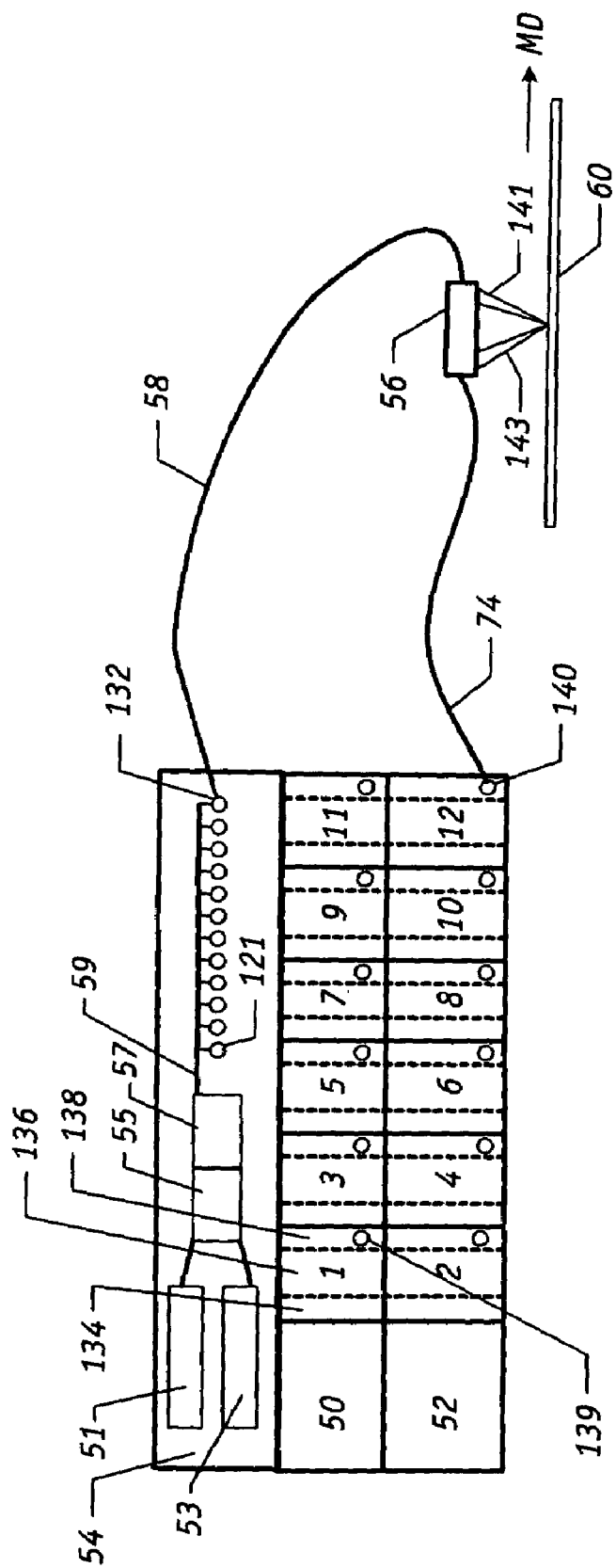

Alternatively as illustrated in FIG. 3, a sensor system requiring only two light sources, e.g., SLEDs, and corresponding measurement and reference wavelength light source controllers but having multiple optical heads can be employed. As shown, the sensor system includes a reference wavelength light source controller 50 and a measurement (or absorption) wavelength light source controller 52 and twelve moisture sensors that are labeled 1 through 12; as is apparent, the sensor system can have fewer or more sensors. Sensor 1 includes pre-amplifier 138 and lockin amplifiers 134 and 136 and an input port 139. Each of the other eleven sensors preferably has the same configuration. The controllers 50 and 52 can control both the temperature and the drive current of the two corresponding SLED sources 51 and 53 that are housed in the fiber optic and optoelectonic compartment 54. The light from the two SLEDs (reference and measurement) are coupled by a single mode optical fiber directional coupler 55 to a single mode optical fiber 57 which in turn is split with splitter 59 and connected to the twelve light output ports, the first and last being illustrated as 121 and 132, respectively.

In this fashion, the output port has access to a portion of the combined light from the reference and measurement SLEDs. Light is simultaneously available on each of the output ports that are located in compartment 54. The light from each of the output ports is a source beam for an individual moisture sensor or optical head. For example, sensor 12 has associated therewith output port 132 and optical head 56. Light is delivered to the optical head 56 through a multimode fiber optic downlead 58. Alternatively a single-mode fiber could be used instead of the multimode fibers for this source downlead 58. The optical head 56 images light 141 from downlead 58 onto a paper sheet 60 using a lens and/or mirror. Light 143 that is scattered from the sheet 60 is captured using another lens and/or mirror and imaged into the receiver fiber 74. This received light is then delivery via input port 140 to the demodulation electronics which includes a receiver port with a photodiode and pre-amplifier and lockin amplifiers of sensor 12 as illustrated. The demodulated output from the two lockin amplifiers is then processed in order to obtain the moisture level in the sheet as measured by sensor 12.

Figure 4:
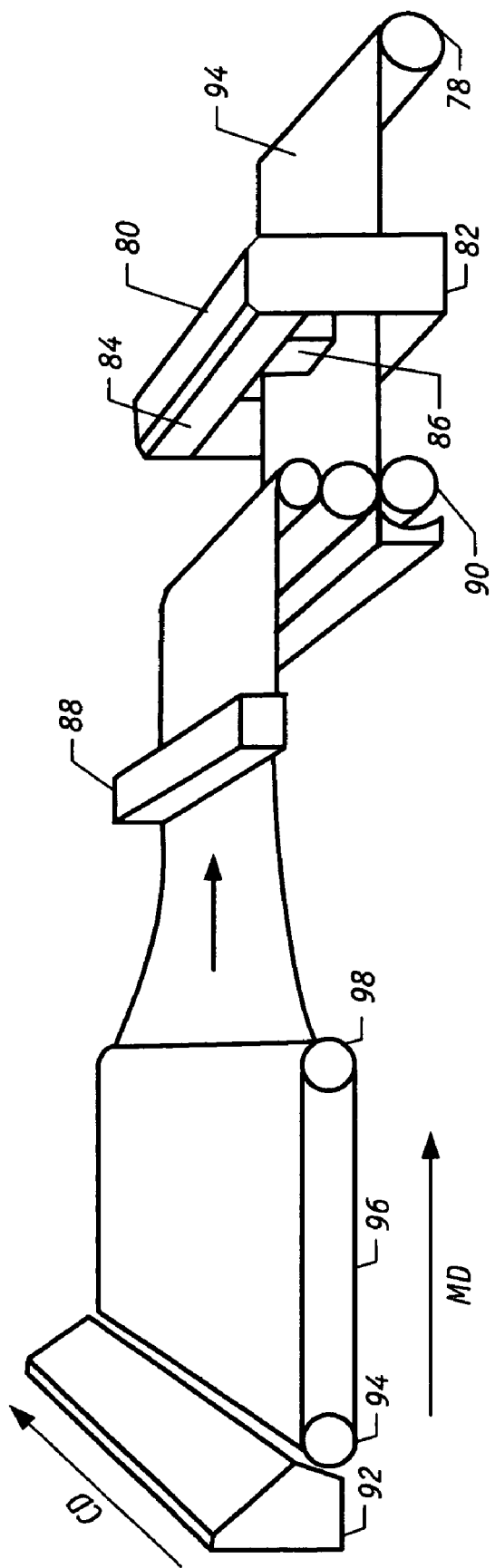
FIG. 4 illustrates a sheetmaking system incorporating the sensor of the present invention.

The inventive sensor can be used to measure physical characteristics of an aqueous mixture (referred to as wetstock) in a sheetmaking system. FIG. 4 shows a typical sheetmaking system for producing a continuous sheet of paper material 94 including a headbox 92, a steambox 88, a calendaring stack 90, a take-up reel 78 and scanner system 80 that includes the inventive sensor. In the headbox 92, actuators are arranged to control discharge of wetstock onto supporting wire or web 96 along the cross direction. The sheet of fibrous material that forms on top of the wire 96 is trained to travel in the machine direction between rollers 94 and 98 and passes through a calendaring stack 90. The calendaring stack 90 includes actuators that control the compressive pressure applied across the paper web. The sheetmaking system includes a press section (not shown) where water is mechanically removed from the sheet and where the web is consolidated. Thereafter, water is removed by evaporation in the dryer section (not shown). The finished sheet product 94 is collected on a reel 78. In practice, the portion of the paper making process near a headbox is referred to as the "wet end", while the portion of the process near a take-up reel is referred to as the "dry end".

The scanner system 80 generally includes pairs of horizontally extending guide tracks 84 that span the width of the paper product 94. The guide tracks are supported at their opposite ends by upstanding stanchions 82 and are spaced apart vertically by a distance sufficient to allow clearance for paper product 94 to travel between the tracks. The sensor is secured to a carriage 86 that moves back-and-forth over to paper product 94 as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein fully by reference.

The sensor system as illustrated in FIG. 3 is particularly suited for measuring moisture levels at multiple locations in the papermaking process in the machine direction. The twelve sensors of the system can be employed, for instance, along the machine direction over the web to optimize papermaking machines to generate a continuous moisture profile of the paper stock on the web which is compared to an "ideal" profile for making a particular grade of paper. Depending on the degree of deviation from ideal, wet end and/or dry end parameters can be adjusted accordingly. A suitable control process is described in U.S. Pat. No. 6,092,003 to Hagart-Alexander which is incorporated herein by reference. While dry end parameters, e.g., temperature of heating devices, can be controlled to achieve the desired final product, typically the wet end parameters are more important. Process control techniques for papermaking machines are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et. al, U.S. Pat. No. 6,080,278 to Heaven et al., U.S. Pat. No. 6,059,931 to Hu et al., U.S. Pat. No. 6,853,543 to Hu et al., and U.S. Pat. No. 5,892,679 to He, which are all incorporated herein by reference.

Spectrometric scanning systems are further described, for instance, U.S. Pat. No. 5,795,394 to Belotserkovsky et al., discloses a scanning reflective-type infrared coating sensor and U.S. Pat. No. 6,404,502 to Preston et al. discloses a reflective-type gloss sensor, both patents are incorporated herein by reference. On-line scanning sensor systems for optically measuring the dry basis weight, basis weight, and moisture content of fibrous sheets during papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein by reference.

A high-speed moisture measuring sensor configured as shown in FIGS. 1 and 2 was constructed using two SLEDs from SuperLumDiodes, Ltd. (Moscow, Russia). A SLED with a nominal center wavelength and full width half maximum linewidth (FWHM) of around 1310 nm and 50 nm, respectively, was used as the reference source and a SLED with a nominal center wavelength and a FWHM of 1480 nm and 50 nm, respectively, was used as the measurement source. These wavelengths were chosen because high power SLED sources are commercially available at these wavelengths and conveniently there is a water absorption peak within the bandwidth of the 1480 nm nominal center wavelength of the measurement SLED. Two laser diode controllers model LCD-3724B from ILX Lightwave (Bozeman, Mont.) were used to control both the drive current and temperatures of the two SLEDs. A sinusoidal modulation was applied to each of the SLED's via the external modulation input on the diode controllers from the internal oscillator in two digital signal processing lock-in amplifiers from Signal Recovery of Advanced Measurement Technology, Inc. (Oak Ridge, Tenn.). In one example the reference and the measure SLED's were modulated at 48 kHz and 24.78 kHz, respectively, however there are many different combinations of modulation frequencies that can be used. Light from the two SLEDs were combined using a 3 dB single-mode fiber optic directional coupler. The two output arms of the directional coupler were then coupled into multimode fiber. These source delivery fibers were terminated at the optical head; the output light from the multimode optical fiber was then imaged onto the paper under test.

A portion of the light that is scattered from the paper was captured by a lens and coupled into a multimode receiving fiber, which was of the same type as the delivery fibers. Note that it is not necessary that the receiver fiber be of the same type as the source fiber. Light from the output end of the receiving fiber was coupled onto an InGaAs PIN photodiode (OSI Fibercomm, Inc. (Hawthorne, Calif.). The output from the photodiode was fed to the transimpedence pre-amplifier and the output of this was then fed to the lock-in amplifiers, which demodulated the reference and measurement signals. The two voltages from the lock-in amplifier were fed to a computer for analysis via a low pass electronic filter that suppressed noise.

Figure 7:
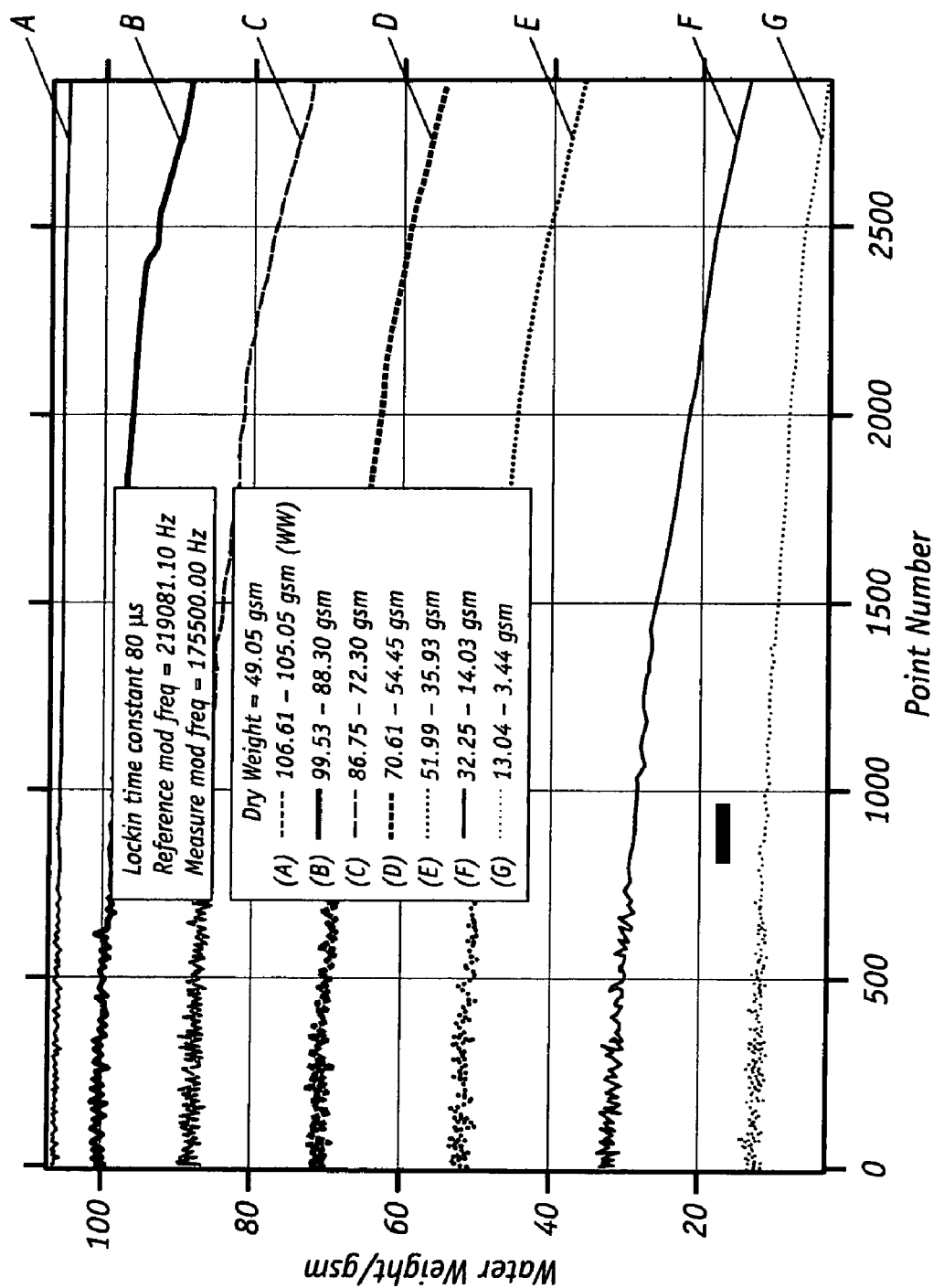
FIG. 7 is a graph of water weight vs. reading number.
Figure 8:
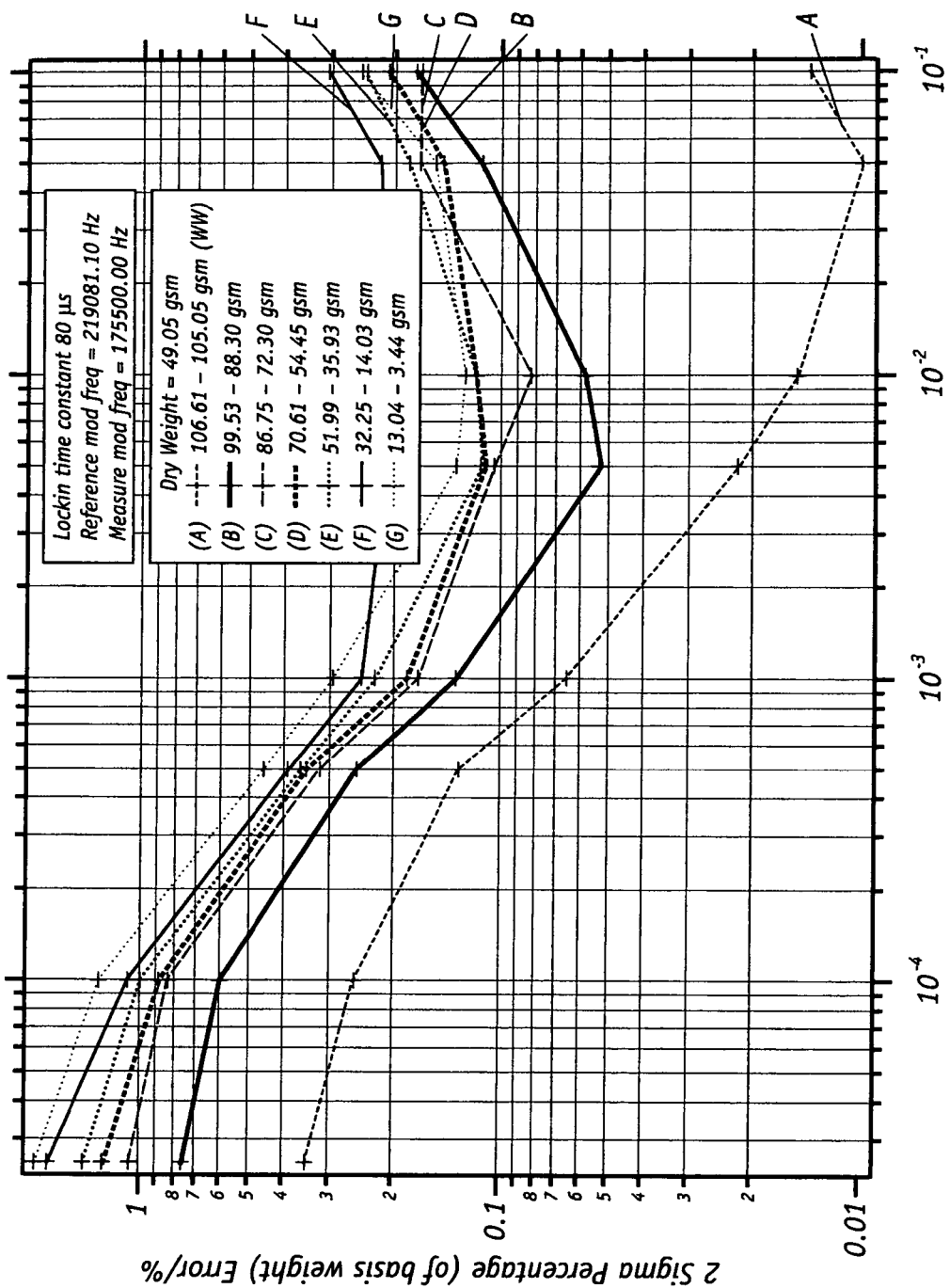
FIG. 8 is a two sigma percentage (of basis weight) error as a function of integration time for the data shown in FIG. 7.

In order to characterize its performance, the sensor was used in repeatability testing by measuring newsprint paper samples at different moisture levels as the samples were drying. Since this was a dynamic sample, the repeatability tests were conducted a number of times to cover the range from approximately 100 gsm water weight (67% moisture) weight to approximately 8 gsm water weight (14% moisture). The newsprint paper had a dry weight moisture content of 49.05 gsm. The measurements were made at ambient temperature and the calculations were implemented with a microprocessor using LABVIEW software from National Instruments (Austin, Tex.). With the inventive sensor, much faster integration times, e.g., sub-microsecond integration times, are possible. FIGS. 7 and 8 show data for a sensor with a bandwidth of 12,500 Hz (80 microseconds). As a comparison, for prior art sensors using QTH light source that were mechanically modulated with choppers that operated at 640 Hz, for instance, the minimum integration time was about 10 ms (100 Hz).

Figure 5:
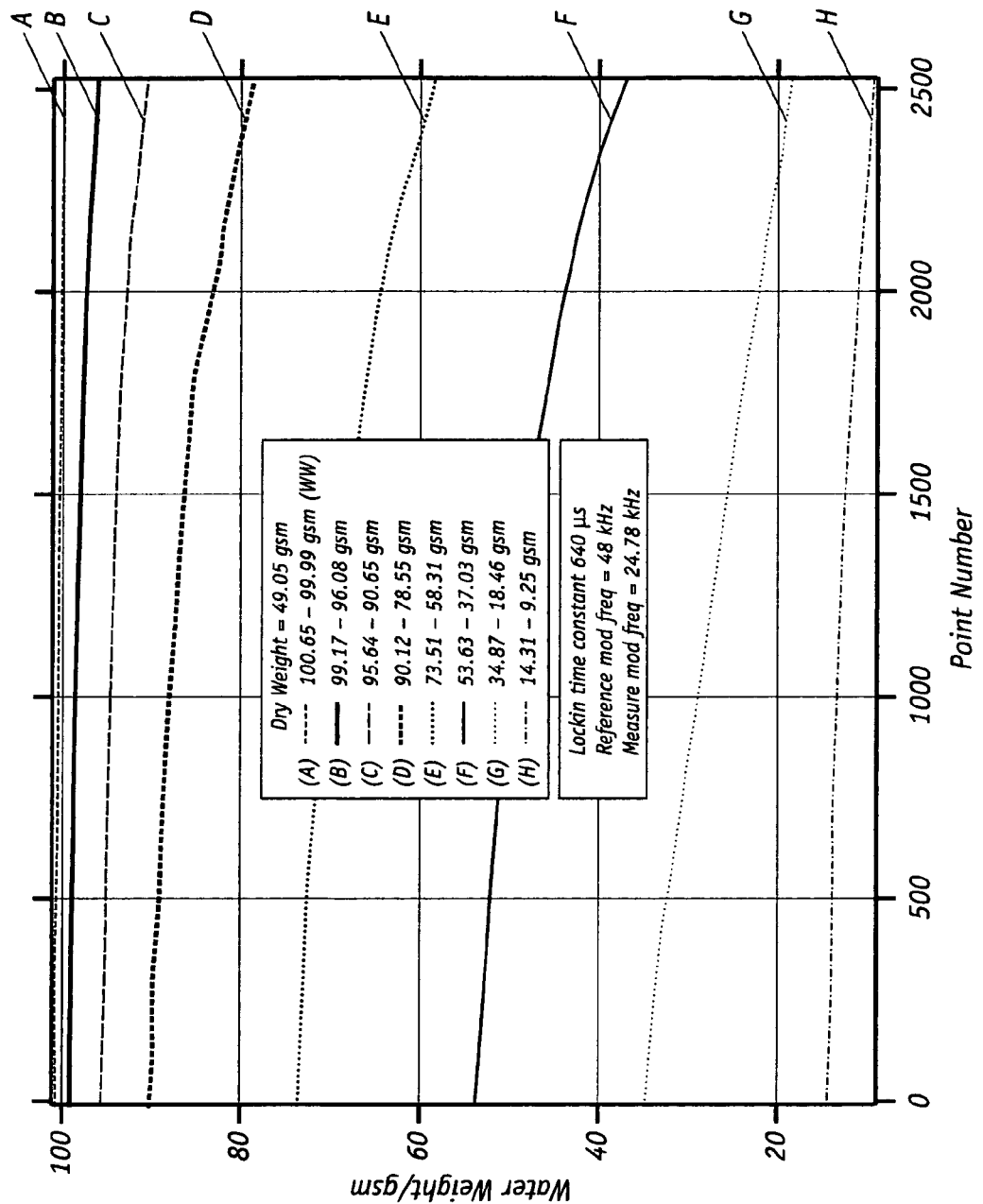
FIG. 5 is a graph of water weight vs. reading number.
Figure 6:
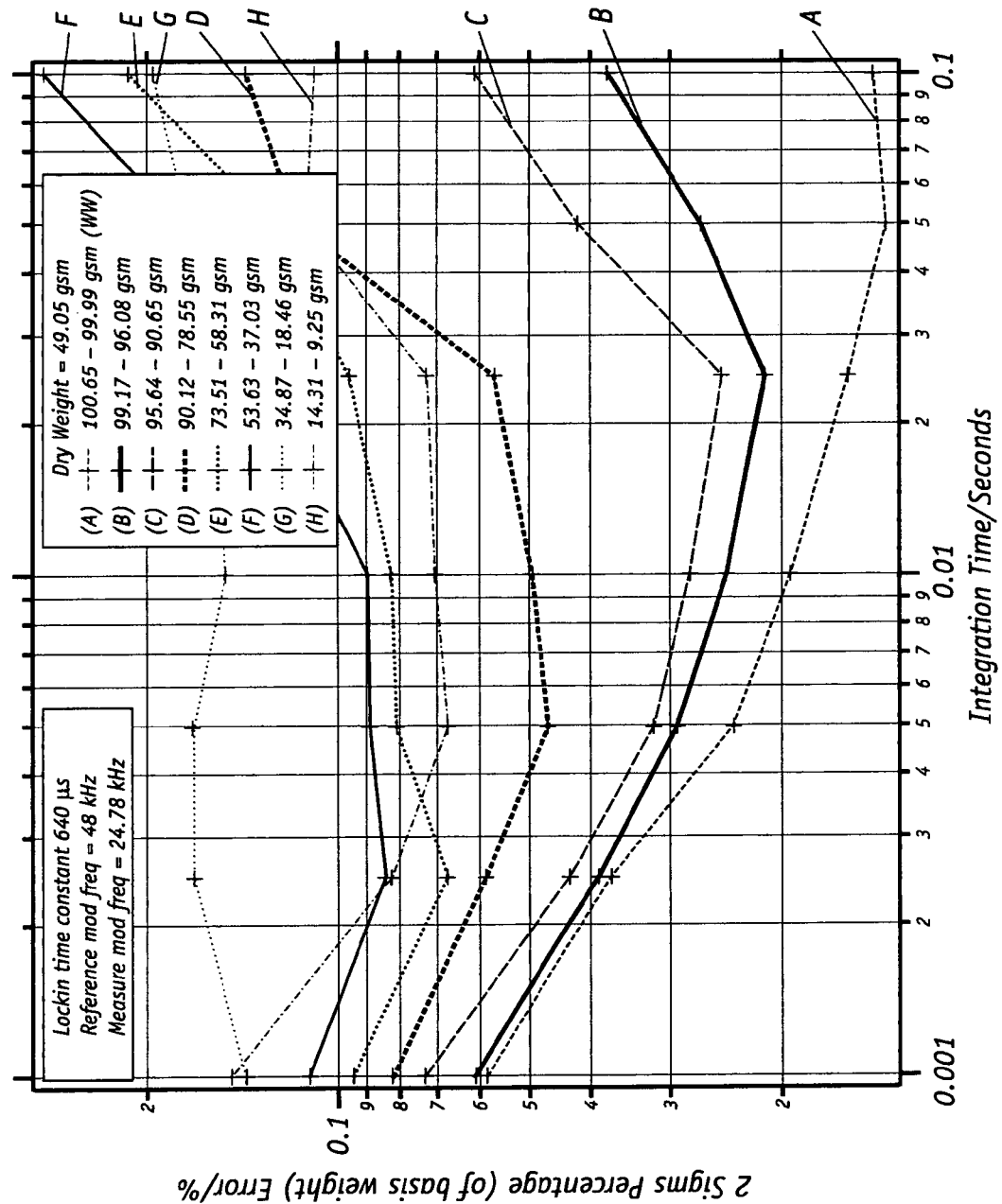
FIG. 6 is a two sigma percentage (of basis weight) error as a function of integration time for the data shown in FIG. 5.

In a first set of tests, the lockin time constant for the sensor was 640 µs and the reference and measurement modulation frequencies were 48 kHz and 24.78 kHz, respectively. The data acquisition (or sampling) rate was 2 kHz and the minimum integration time was 500 µs. In this experiment, the water content of the paper was measured as the paper dried. During this period, the moisture content decreased from 100.65 to 9.25 gsm. FIG. 5 shows eight separate data sets of water weight readings (labeled A to H) as a function of reading number (equivalent to time). FIG. 6 shows the two sigma repeatability results as a function of integration time. It can be seen from FIG. 6 that the two sigma repeatability for an approximately 60% moisture sample is around 0.095% (or 0.12 gsm of water weight) for a 1 ms integration time.

In a second set of tests, the lockin time constant for the sensor was 80 µs and the reference and measurement modulation frequencies were 219,081.10 Hz and 175500.00 Hz, respectively. The data acquisition rate was 50 kHz and the integration time was 25 µs. In this experiment, the water content of the paper was measured as the paper dried from 100.65 to 3.44 gsm. FIG. 7 shows seven separate data sets of water weight readings (labeled A to G) as a function of reading number (or time). FIG. 8 shows a two sigma repeatability of approximately 1.2% (for approximately 60% moisture) and at an integration time of 1 ms we have a two sigma repeatability of approximately 0.2% (for approximately 60% moisture).

While the two sigma results for the 80 μs time constant are no better than those of the 640 μs time constant, the system had eight times higher bandwidth and can therefore respond faster to moisture changes. This means that a sensor can be scanned faster. It should be noted from the repeatability curves that the log-log plots are not linear; the reason is that by frequency division multiplexing the light sources, the electronic noise was no longer random white noise in nature and has definite spectral content due to the mixing of the reference and measure source modulation frequencies and their harmonics.

It should be noted that sensor bandwidths much higher than those presented in these experiments are possible. The bandwidths employed were limitations of the particular equipment used in the experiments and are not intended to limit the scope of the present invention.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A sensor for measuring at least one selected component in a composition, comprising:
   at least one light source operable to generate light having a desired wavelength range;
   a controller operable to modulate the at least one light source without mechanically modulating the at least one light source;
   a detector operable to receive and measure light that emerges from the composition;
   an optical head comprising first optics operable to direct the light from the at least one light source to the composition and second optics operable to direct the light that emerges from the composition to the detector, wherein the first and second optics comprise first and second mirrors, respectively, and wherein the light from the at least one light source is transmitted through an optical fiber to the optical head; and
   a signal analyzer operable to analyze measurements of the light that emerges from the composition and to correct for bend loss in the optical fiber.

2. The sensor of claim 1, wherein the at least one light source comprises at least one of: a superluminescent light-emitting diode and a laser diode.

3. The sensor of claim 1, wherein the controller is operable to directly modulate a drive current of the at least one light source.

4. The sensor of claim 1, wherein the controller is operable to employ one or more external electro-optical modulators.

5. The sensor of claim 1, wherein the controller is operable to employ one or more external acousto-optical modulators.

6. The sensor of claim 1, wherein the controller is operable to modulate the at least one light source at a rate of at least 5 kHz.

7. The sensor of claim 1, wherein the at least one light source comprises a light emitting device coupled to the optical fiber so that light from the light emitting device is transmitted through the optical fiber to the optical head.

8. The sensor of claim 7, wherein the optical head further comprises a coupler operable to be coupled to the optical fiber.

9. The sensor of claim 1, wherein:
   the optical head is configured to move; and
   further comprising a cable take-up mechanism configured to manage the optical fiber to preserve an overall bend length and radius of the optical fiber.

10. The sensor of claim 1, wherein:
    the detector is operable to generate a signal that is proportional to an intensity of the light received; and
    the sensor further comprises a filter operable to filter noise from the signal.

11. The sensor of claim 10, wherein the filter comprises lockin amplifiers operable to amplify a modulated signal and to convert the modulated signal to a proportionate DC level signal while simultaneously suppressing the noise with a low-pass filter.

12. The sensor of claim 11, wherein the lockin amplifiers are operable to remove background noise.

13. The sensor of claim 1, wherein no optical filter is used to generate the light having the desired wavelength range.

14. A sensor for measuring at least one selected component in a composition, comprising:
    a first light source operable to generate first light having a first wavelength region that is sensitive to the at least one selected component;
    a first controller operable to modulate the first light source without mechanically modulating the first light source;
    a second light source operable to generate second light having a second wavelength region that has a different sensitivity to the at least one selected component;
    a second controller operable to modulate the second light source without mechanically modulating the second light source;
    a detector operable to receive and measure third light that emerges from the composition, the third light based on the first light and the second light; and
    a signal analyzer operable to analyze measurements of the third light, wherein the first light and the second light are directed at the composition through an optical fiber, and wherein the signal analyzer is operable to use measurements associated with a portion of the third light that is based on the second light to correct for bend loss in the optical fiber.

15. The sensor of claim 14, wherein:
    the first controller is operable to modulate the first light source at a first frequency to generate a first modulated light signal; and
    the second controller is operable to modulate the second light source at a second frequency to generate a second modulated light signal, wherein the first frequency is different from the second frequency.

16. The sensor of claim 15, wherein the first modulated light signal is multiplexed with the second modulated light signal for transmission through the optical fiber.

17. The sensor of claim 16, wherein frequency division multiplexing is employed to multiplex the first and second modulated light signals.

18. The sensor of claim 15, wherein the detector comprises a single detector and a single pre-amplifier operable to detect light having the first frequency and the second frequency.

19. The sensor of claim 14, wherein:
the first light source comprises a first light emitting device coupled to the optical fiber so that the first light from the first light emitting device is transmitted through the optical fiber; and
the second light source comprises a second light emitting device coupled to the optical fiber so that the second light from the second light emitting device is transmitted through the optical fiber.

20. An apparatus for measuring at least one selected component in a composition, comprising:
at least one light source operable to generate light having a desired wavelength range;
a splitter operable to split the light from the at least one light source and to deliver the light to a plurality of positions on the composition;
a controller operable to modulate the at least one light source without mechanically modulating the at least one light source and to adjust operation of the at least one light source to account for temperature-dependent wavelength shifting associated with variations in a temperature of the composition; and
a plurality of detectors operable to receive light that emerges from the composition at the plurality of positions.

21. The apparatus of claim 20, wherein:
the at least one light source comprises:
a first light source operable to generate first light having a first wavelength region that is sensitive to the component; and
a second light source operable to generate second light having a second wavelength region that has a different sensitivity to the component; and
the controller comprises:
a first controller operable to modulate the first light source without mechanically modulating the first light source; and
a second controller operable to modulate the second light source without mechanically modulating the second light source.

22. The apparatus of claim 21, wherein:
the first controller is operable to modulate the first light source at a first frequency to generate a first modulated light signal; and
the second controller is operable to modulate the second light source at a second frequency to generate a second modulated light signal, wherein the first frequency is different from the second frequency.

23. The apparatus of claim 22, wherein the first modulated light signal is multiplexed with the second modulated light signal for transmission through an optical fiber.

24. The apparatus of claim 23, wherein frequency division multiplexing is employed to multiplex the first and second modulated light signals.

25. A method for sensing a substance in a composition, comprising the steps of:
irradiating the composition with radiation including wavelengths in at least first and second separate wavelength regions, wherein the radiation is provided by one or more light sources that are modulating non-mechanically, and wherein the radiation in the first wavelength region is more sensitive to the substance in the composition than the radiation in the second wavelength region;
detecting an amount of radiation that emerges from the composition in the first and second separate wavelength regions; and
adjusting operation of the one or more light sources to account for temperature-dependent wavelength shifting associated with variations in a temperature of the composition.

26. The method of claim 25, wherein the irradiating step comprises irradiating the composition with a first modulated light signal that is modulated at a first frequency and a second modulated light signal that is modulated at a second frequency, the second frequency different from the first frequency.

27. The method of claim 26, wherein the first modulated light signal is multiplexed with the second modulated light signal for transmission through an optical fiber.

28. The method of claim 27, wherein frequency division multiplexing is employed to multiplex the first and second modulated light signals.

29. The method of claim 25, further comprising the step of computing an amount of the substance in the composition based upon the detected amount of radiation in the first and second wavelength regions.

30. The method of claim 25, wherein the composition is a flat sheet product that comprises at least one of: paper and plastic.

31. The method of claim 25, wherein:
the composition comprises paper; and
a level of water in the paper is computed.

* * * * *